United States Patent [19]

Whitcomb et al.

[11] Patent Number: 5,466,804
[45] Date of Patent: Nov. 14, 1995

[54] SILVER-CARBOXYLATE/1,2-DIAZINE COMPOUNDS AS SILVER SOURCES IN PHOTOTHERMOGRAPHIC AND THERMOGRAPHIC ELEMENTS

[75] Inventors: David R. Whitcomb, Woodbury; William C. Frank, Roseville, both of Minn.

[73] Assignee: Minnesota Mining and Manufacturing, Saint Paul, Minn.

[21] Appl. No.: 254,552

[22] Filed: Jun. 6, 1994

Related U.S. Application Data

[62] Division of Ser. No. 183,486, Jan. 19, 1994, Pat. No. 5,350,669.

[51] Int. Cl.⁶ .............................. C07F 1/10; G03C 1/498
[52] U.S. Cl. .................................................. 544/225
[58] Field of Search ............................................ 544/225

[56] References Cited

U.S. PATENT DOCUMENTS

| | | | |
|---|---|---|---|
| 3,180,731 | 4/1965 | Roman et al. | 96/29 |
| 3,457,075 | 7/1969 | Morgan et al. | 96/67 |
| 3,531,286 | 9/1970 | Renfrew | 96/67 |
| 3,761,270 | 9/1973 | Mauriae et al. | 96/77 |
| 3,839,049 | 10/1974 | Simons | 96/114.6 |
| 3,846,136 | 11/1974 | Sullivan | 96/114.1 |
| 3,994,732 | 11/1976 | Winslow | 96/114.1 |
| 4,021,240 | 5/1977 | Cerquone et al. | 96/29 D |
| 4,021,249 | 5/1977 | Noguchi et al. | 96/114.1 |
| 4,022,617 | 5/1977 | McGuckin | 96/29 D |
| 4,187,108 | 5/1980 | Willis | 430/203 |
| 4,260,677 | 4/1981 | Winslow et al. | 430/618 |
| 4,374,921 | 2/1983 | Frenchik | 430/338 |
| 4,384,117 | 5/1983 | Wysor | 544/225 |
| 4,426,441 | 1/1984 | Adin et al. | 430/351 |
| 4,460,681 | 7/1984 | Frenchik | 430/502 |
| 4,883,747 | 11/1989 | Grieve et al. | 430/542 |

OTHER PUBLICATIONS

T. Tsuda, S. Ohba, M. Takahashi and M. Ito, *Acta Cryts.*, 1989, C45, 887–890.

J. J. Porter, J. L. Murray, and K. B. Takvorian, *J. Heterocyclic Chem.* 1973, 10, 43.

Primary Examiner—Mark L. Berch
Attorney, Agent, or Firm—Gary L. Griswold; Walter N. Kirn; Gregory A. Evearitt

[57] ABSTRACT

Novel silver-carboxylate/1,2-diazine compounds having the formula:

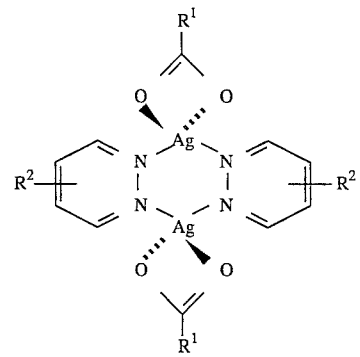

wherein:

$R^1$ represents either an alkyl, aralkyl, cycloalkyl, or alkenyl group of up to 29 carbon atoms; or an aryl group of up to 14 carbon atoms; and and $R^2$ represents either hydrogen, an alkyl group, a cycloalkyl group fused to the 1,2-diazine ring, or the atoms necessary to complete a 5- or 6-membered aromatic ring fused to the 1,2-diazine ring.

The novel silver-carboxylate/1,2-diazine compounds are coordination compounds of two silver-carboxylate molecules and two molecules comprising a 1,2-diazine nucleus. These compounds can serve as the silver source in a black-and-white thermographic or photothermographic element or as the oxidizing agent for a dye-based thermographic or photothermographic color-imaging construction.

4 Claims, No Drawings

SILVER-CARBOXYLATE/1,2-DIAZINE COMPOUNDS AS SILVER SOURCES IN PHOTOTHERMOGRAPHIC AND THERMOGRAPHIC ELEMENTS

This is a division of application Ser. No. 08/183,486 filed Jan. 19, 1994, now U.S. Pat. No. 5,350,699.

BACKGROUND OF THE INVENTION

1. Field of the Invention

This invention relates to novel coordination compounds of silver for use in black-and-white and color thermographic and photothermographic imaging elements and to thermographic and photothermographic elements employing these materials.

2. Background of the Art

Silver halide-containing photothermographic imaging materials (i.e., heat-developable photographic elements) processed with heat, and without liquid development, have been known in the art for many years. These materials, also known as "dry silver" compositions or emulsions, generally comprise a support having coated thereon: (1) a photosensitive material that generates elemental silver when irradiated; (2) a non-photosensitive, reducible silver source; and (3) a reducing agent for the non-photosensitive reducible silver source; and (4) a binder. The photosensitive material is generally photographic silver halide which must be in catalytic proximity to the non-photosensitive, reducible silver source. Catalytic proximity requires an intimate physical association of these two materials so that when silver specks or nuclei are generated by the irradiation or light exposure of the photographic silver halide, those nuclei are able to catalyze the reduction of the reducible silver source. It has long been understood that elemental silver ($Ag^°$) is a catalyst for the reduction of silver ions, and the photosensitive photographic silver halide may be placed into catalytic proximity with the non-photosensitive, reducible silver source in a number of different fashions, such as by partial metathasis of the reducible silver source with a halogen-containing source (see, for example, U.S. Pat. No. 3,457,075); coprecipitation of silver halide and reducible silver source material (see, for example, U.S. Pat. No. 3,839,049); and other methods that intimately associate the photosensitive photographic silver halide and the non-photosensitive, reducible silver source.

The non-photosensitive, reducible silver source is a material that contains silver ions. The preferred non-photosensitive, reducible silver source comprises silver salts of long chain aliphatic carboxylic acids, typically having from 10 to 30 carbon atoms. The silver salt of behenic acid or mixtures of acids of similar molecular weight are generally used. Salts of other organic acids or other organic materials, such as silver imidazolates, have been proposed, and U.S. Pat. No. 4,260,677 discloses the use of complexes of inorganic or organic silver salts as non-photosensitive, reducible silver sources.

In both photographic and photothermographic emulsions, exposure of the photographic silver halide to light produces small clusters of silver atoms ($Ag^°$). The imagewise distribution of these clusters is known in the art as a latent image. This latent image generally is not visible by ordinary means and the photosensitive emulsion must be further processed in order to produce a visible image. The visible image is produced by the reduction of silver ions, which are in catalytic proximity to silver halide grains bearing the clusters of Silver atoms, i.e. the latent image. This produces a black-and-white image.

As the visible image is produced entirely by elemental silver ($Ag^°$), one cannot readily decrease the amount of silver in the emulsion without reducing the maximum image density. However, reduction of the amount of silver is often desirable in order to reduce the cost of raw materials used in the emulsion.

One method of attempting to increase the maximum image density in black-and-white photographic and photothermographic emulsions without increasing the amount of silver in the emulsion layer is by incorporating toning agents into the emulsion. Toning agents improve the color of the silver image of the photothermographic emulsions, as described in U.S. Pat. Nos. 3,846,136; 3,994,732; and 4,021,249.

Another method of increasing the maximum image density of photographic and photothermographic emulsions without increasing the amount of silver in the emulsion layer is by incorporating dye-forming materials in the emulsion. For example, color images can be formed by incorporation of leuco dyes into the emulsion. Leuco dyes are the reduced form of a color-bearing dye. Upon imaging, the leuco dye is oxidized, and the color-bearing dye and a reduced silver image are simultaneously formed in the exposed region. In this way a dye enhanced silver image can be produced, as shown, for example, in U.S. Pat. Nos. 3,531,286; 4,187,108; 4,426,441; 4,374,921; and 4,460,681.

Multicolor photothermographic imaging articles typically comprise two or more monocolor-forming emulsion layers (often each emulsion layer comprises a set of bilayers containing the color-forming reactants) maintained distinct from each other by barrier layers. The barrier layer overlaying one photosensitive, photothermographic emulsion layer typically is insoluble in the solvent of the next photosensitive, photothermographic emulsion layer. Photothermographic articles having at least 2 or 3 distinct color-forming emulsion layers are disclosed in U.S. Pat. Nos. 4,021,240 and 4,460,681. Various methods to produce dye images and multicolor images with photographic color couplers and leuco dyes are well known in the art as represented by U.S. Pat. Nos. 4,022,617; 3,531,286; 3,180,731; 3,761,270; 4,460,681; 4,883,747; and *Research Disclosure*, March 1989, item 29963.

Thermographic imaging constructions (i.e., heat-developable materials) processed with heat, and without liquid development, are widely known in the imaging arts and rely on the use of heat to help produce mi image. These elements generally comprise a support or substrate (such as paper, plastics, metals, glass, and the like) having coated thereon: (1) a thermally-sensitive, reducible silver source; (2) a reducing agent for the thermally-sensitive, reducible silver source; and (3) a binder.

In a typical thermographic construction, the image-forming layers are based on silver salts of long chain fatty acids, such as silver behenate. At elevated temperatures, silver behenate is reduced by a reducing agent for silver ion such as methyl gallate, hydroquinone, substituted-hydroquinones, hindered phenols, catechol, pyrogallol, ascorbic acid, ascorbic acid derivatives, and the like, whereby an image comprised of elemental silver is formed. When the reducing agent is a material that can be oxidized to form or release a dye, as, for example, a leuco dye, a colored image is formed.

Many times, the thermographic construction is brought into contact with the thermal head of a thermographic recording apparatus, such as a thermal printer, thermal facsimile, and the like. In such instances, an anti-stick layer is coated on top of the imaging layer to prevent sticking of the thermographic construction to the thermal head of the apparatus utilized. The resulting thermographic construction is then heated to an elevated temperature, typically in the range of about 60°–25° C., resulting in the formation of an image.

Phthalazine (PHi), (i.e., 4,5-benzo-1,2-diazine), is known as a toner and added to photothermographic formulations. There are no rapore of polymeric silver-carboxylate/PHZ coordination compounds, however. The compound $Ag(PHZ)_2NO_3$ is reported in T. Tsuda, S. Ohba, M. Takahashi and M. Ito, *Acta Cryts.* 1989, C45, 887. A similar compound, $Ag(PHZ)NO_3$, complex having a 1:1 Ag:PHZ ratio is described in J. J. Porter, J. L. Murray, and K. B. Takvorian *J. Helemcyclic Chem.* 1973, 10, 43.

SUMMARY OF THE INVENTION

In accordance with one embodiment of the present invention, new silver-carboxylate/1,2-diazine compounds have been discovered. These silver-carboxylate/1,2-diazine compounds are coordination complexes of two silver-carboxylate molecules and two molecules comprising a 1,2-diazine nucleus. These compounds, herein referred to as silver carboxylate/1,2-diazine compounds, can serve as the silver source in a black-and-white thermographic or photothermographic element or as the oxidizing agent for a dye-based thermographic or photothermographic color-imaging construction.

The silver-carboxylate/1,2-diazine compounds can be represented by the following formula:

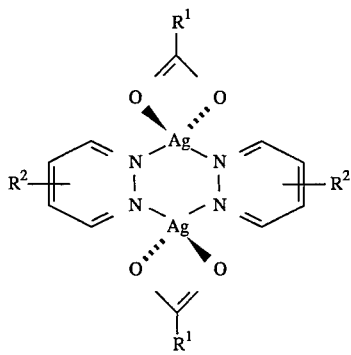

(I)

wherein:

- $R^1$ represents either an alkyl, aralkyl, cycloalkyl, or alkenyl group of up to 29 carbon atoms; preferably of from 9 to 29 carbon atoms; and most preferably of from 14 to 27 carbon atoms; or an aryl group of up to 14 carbon atoms, preferably of up to 10 carbon atoms;

- and $R^2$ represents either hydrogen, an alkyl group, a cycloalkyl group fused to the 1,2-diazine ring, or the atoms necessary to complete a 5- or 6-membered aromatic ring fused to the 1,2-diazine ring and preferably represents the atoms necessary to complete a 5- or 6-membered aromatic ring fused to the 1,2-diazine ring.

In another embodiment, the present invention provides heat-developable, photothermographic elements capable of providing stable, high density images of high resolution. These elements comprise a support bearing at least one photosensitive, image-forming, photothermographic emulsion layer comprising:

(a) a photosensitive silver halide;

(b) a non-photosensitive, reducible source of silver comprising a silver-carboxylate/ 1,2-diazine compound of formula (I);

(c) a reducing agent for the non-photosensitive, reducible source of silver; and (d) a binder.

In still another embodiment, the present invention comprises a thermographic construction comprising a substrate coated with an imaging layer comprising:

(a) a non-photosensitive, reducible source of silver comprising a silver-carboxylate- 1,2-diazine compound of formula (I);

(b) a reducing agent for the non-photosensitive, reducible source of silver; and (c) a binder.

In both the inventive thermographic and photothermographic constructions, the reducing agent for the non-photosensitive silver source may optionally comprise a compound capable of being oxidized to form a dye or to release a pre-formed dye. Preferably, the dye-forming material is a leuco dye.

As is well understood in this technical area, a large degree of substitution is not only tolerated, but is often advisable. As a means of simplifying the discussion and recitation of certain terminology used throughout this application, the terms "group" and "moiety" are used to differentiate between chemical species that allow for substitution or which may be substituted and those which do not so allow or may not be so substituted. Thus, when the term "group" is used to describe a chemical substituent, the described chemical material includes the basic group and that group with conventional substitution. Where the term "moiety" is used to describe a chemical compound or substituent, only an unsubstituted chemical material is intended to be included. For example, the phrase "alkyl group" is intended to include not only pure open-chain and cyclic saturated hydrocarbon alkyl substituents, such as methyl, ethyl, propyl, t-butyl, cyclohexyl, adamantyl, octadecyl, and the like, but also alkyl substituents bearing further substituents known in the art, such as hydroxyl, alkoxy, vinyl, phenyl, halogen atoms (F, Cl, Br, and I), cyano, nitro, amino, carboxyl, etc. On the other hand, the phrase "alkyl moiety" is limited to the inclusion of only pure open-chain and cyclic saturated hydrocarbon alkyl substituents, such as methyl, ethyl, propyl, t-butyl, cyclohexyl, adamantyl, octadecyl, and the like.

Other aspects, advantages, and benefits of the present invention are apparent from the detailed description, the examples, and the claims.

DETAILED DESCRIPTION OF THE INVENTION

A new class of silver compounds have been discovered which are useful as a unique source of the silver oxidant in black-and-white (B&W) thermographic and photothermographic materials. These are comprised of coordination compounds of silver-carboxylate/1,2-diazine compounds having the following formula:

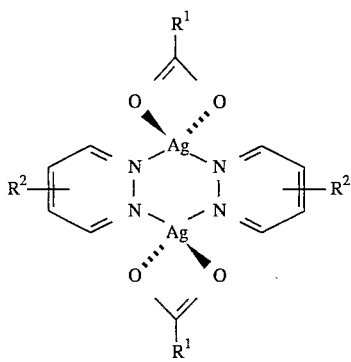

(I)

In formula (I), $R^1$ is either an alkyl, aralkyl, cycloalkyl, or alkenyl group of up to 29 carbon atoms, preferably of from 9 to 29 carbon atoms, and most preferably of from 14 to 27 carbon atoms; or an aryl group of up to 14 carbon atoms, preferably of up to 10 carbon atoms.

In formula (I), $R^2$ represents either hydrogen, an alkyl group, a cyoloalkyl group fused to the 1,2-diazine ring, or the atoms necessary to complete a 5- or 6-membered aromatic ring fused to the 1,2-diazine ring.

The photosensitive element of the present invention comprises a support having at least one photosensitive image-forming, photothermographic emulsion layer comprising:

(a) a photosensitive silver halide, (b) a non-photosensitive, reducible source of silver comprising a silver-carboxylate/ 1, 2-diazine compound of formula (I);

(c) a reducing agent for the non-photosensitive, reducible source of silver; and (d) a binder.

In another embodiment, the present invention comprises a thermographic construction comprising a substrate coated with an imaging layer comprising:

(a) a non-photosensitive, reducible source of silver comprising a silver-carboxylate/ 1,2-diazine compound of formula (I);

(b) a reducing agent for the non-photosensitive, reducible source of silver; and (c) a binder.

In both the inventive thermographic and photothermographic constructions, the reducing agent for the non-photosensitive silver source may optionally comprise a compound capable of being oxidized to form a dye or to release a pre-formed dye. Preferably, the dye-forming material is a leuco dye.

The silver-carboxylate/1,2-diazine coordination compounds of the present invention can be made according to methods of synthetic inorganic chemistry which will be apparent to those of ordinary skill in the art. The compounds are prepared by reaction of two molecules of a silver salt of an organic acid (i.e. a silver-carboxylate), particularly the silver salt of a long chain fatty carboxylic acid, wherein the chain typically contains 10 to 30, and preferably 15 to 28, carbon atoms, with two molecules of a compound comprising a 1,2-diazine nucleus. The preparation of such compounds is also detailed later in this application in Example 1. The silver-carboxylate/ 1,2-diazine compounds of the invention are believed to have formula (I) shown above. In formula (I), two molecules having a 1,2-diazine nucleus are coordinated to two molecules of a silver carboxylate. As used in this application, the phrase "1,2-diazine nucleus" is meant to denote any molecule having a 6-membered aromatic ring containing a —N=N—, (or its resonance equivalent, =N—N=) aromatic $sp^2$ moiety.

Non-limiting preferred examples of molecules having a 1,2-diazine nucleus useful in this invention are; 1,2-diazine(pyridazine); 3,4-benzo-1,2-diazine (cinnoline); 4,5-benzo-1,2-diazine (phthalazine-PHZ); and 3,4,5,6-dibenzo-1,2-diazine (benzo[c]cinnoline). The structures of these compounds are shown below. Most preferred are molecules having a 4,5-benzo-1,2-diazine (phthalazine-PHZ) nucleus.

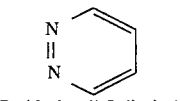
Pyridazine (1,2-diazine)

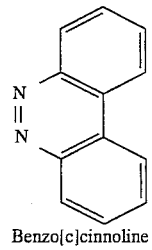
Benzo[c]cinnoline

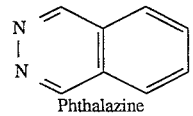
Phthalazine

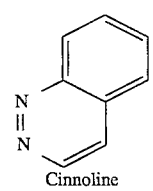
Cinnoline

The structure of a crystal of $Ag_2(O_2CCH_3)_2(PHZ)_2$, determined by X-ray diffraction, indicates it to be made up of individual molecules of $Ag_2(O_2CCH_3)_2(PHZ)_2$ stacked one above the other. The distance between individual atoms indicates each silver to be 5-coordinate, by coordination to an oxygen of a carboxylate of an adjacent $Ag_2(O_2CCH_3)_2(PHZ)_2$ molecule in addition to the carboxylate to which it is attached. In the $Ag_2(O_2CCH_3)_2(PHZ)_2$ molecule itself, there are two molecules of water present in the unit cell. It is assumed that preferred molecules of the present invention derived from longer chain carboxylic acids have a similar crystal structure. However, they may lack water molecules within the crystal.

The photothermographic elements of this invention may be used to prepare black-and-white, monochrome, or full color images. The photothermographic element of this invention can be used, for example, in conventional black-and-white or color photothermographic, in electronically-generated black-and-white or color hardcopy recording, in the graphic arts area, and in digital color proofing. The element of this invention provides high photographic speed, provides strongly absorbing black-and-white or color images, and provides a dry and rapid process.

The thermographic elements of this invention can also be used to prepare to prepare black-and-white or monochrome images.

The Photosensitive Silver Halide

As noted above, when used in a photothermographic construction, the present invention comprises a photosensitive silver halide. The photosensitive silver halide can be any photosensitive silver halide, such as silver bromide, silver iodide, silver chloride, silver bromoiodide, silver chlorobromoiodide, silver chlorobromide, silver chloroiodide, etc. The photosensitive silver halide can be added to the emulsion layer in any fashion so long as it is placed in catalytic proximity to the organic silver compound which serves as a source of reducible silver.

The light sensitive silver halide used in the present invention can be employed in a range of 0.005 mole to 0.5 mole and, preferably, from 0.01 mole to 0.15, mole per mole of silver salt.

The silver halide used in the present invention may be employed without modification. However, it can be chemically and spectrally sensitized in a manner similar to that used to sensitize conventional wet process silver halide or state-of-the-art heat-developable photographic constructions. For example, it may be chemically sensitized with a chemical sensitizing agent such as a compound containing sulfur, selenium or tellurium etc., or a compound containing gold, platinum, palladium, ruthenium, rhodium or iridium, etc., a reducing agent such as a tin halide, etc., or a combination thereof. The details of these procedures are described in T. H. James, *The Theory of the Photographic Process*, Fourth Edition, Chapter 5, pages 149 to 169. Suitable chemical sensitization procedures are also described in Shepard, U.S. Pat. No. 1,623,499; Waller, U.S. Pat. No. 2,399,083; McVeigh, U.S. Pat. No. 3,297,447; and Dunn, U.S. Pat. No. 3,297,446.

The photosensitive silver halides may be spectrally sensitized with various known dyes that spectrally sensitize silver halide. Non-limiting examples of sensitizing dyes that can be employed include cyanine dyes, merocyanine dyes, complex cyanine dyes, complex merocyanine dyes, holopolar cyanine dyes, hemicyanine dyes, styryl dyes, and hemioxanol dyes. Of these dyes, cyanine dyes, merocyanine dyes, and complex merocyanine dyes are particularly useful.

An appropriate amount of sensitizing dye added is generally in the range of from about $10^{-10}$ to $10^{-1}$ mole, and preferably from about $10^{-8}$ to $10^{-3}$ moles, per mole of silver halide.

The Non-Photosensitive Reducible Silver Source Material

When used in photothermographic and thermographic constructions the present invention comprises a non-photosensitive reducible silver source material.

In addition to the a silver-carboxylate/1,2-diazine coordination compound, auxiliary non-photosensitive organic silver salts that can be used in the present invention are silver salts which are comparatively stable to light and which form a silver image by reacting with a reducing agent.

The auxiliary non-photosensitive, reducible silver source can be any material that contains a source of reducible silver ions. Silver salts of organic acids, particularly silver salts of long chain fatty carboxylic acids, are preferred. The chains typically contain 10 to 30, preferably 15 to 28, carbon atoms.

When used in photothermographic elements, the silver halide and the organic silver salt that form a starting point of development should be in reactive association (i.e., in the same layer, in adjacent layers, or layers separated from each other by an intermediate layer having a thickness of less than 1 micron). It is preferred that the silver halide and the organic silver salt are present in the same layer.

Non-limiting examples of such auxiliary silver salts include silver salts of organic compounds having a carboxyl group. Preferred examples thereof include a silver salt of an aliphatic carboxylic acid and a silver salt of an aromatic carboxylic acid. Preferred examples of the silver salts of aliphatic carboxylic acids include silver behenate. silver stearate, silver oleate, silver laureate, silver caprate, silver myristate, silver palmitate, silver maleate, silver fumarate, silver tartrate, silver fumarate, silver linoleate, silver butyrate and silver camphorate, mixtures thereof, etc. Silver salts which are substitutable with a halogen atom or a hydroxyl group can also be effectively used. Preferred examples of the silver salts of aromatic carboxylic acid and other carboxyl group-containing compounds include silver benzoate, a silver substituted benzoate such as silver 3,5-dihydroxybenzoate, silver o-methylbenzoate, silver m-methylbenzoate, silver p-methylbenzoate, silver 2,4-dichlorobenzoate, silver acetamidobenzoate, silver p-phenylbenzoate, etc., silver gallate, silver tannate, silver phthalate, silver terephthalate, silver salicylate, silver phenylacetate, silver pyromellilate, a silver salt of 3-carboxymethyl-4-methyl-4-thiazoline-2-thione or the like as described in U.S. Pat. No. 3,785,830, and silver salt of an aliphatic carboxylic acid containing a thioether group as described in U.S. Pat. No. 3,330,663.

Auxiliary silver salts of compounds containing mercapto or thione groups and derivatives thereof can be used. Preferred examples of these compounds include a silver salt of 3-mercapto-4-phenyl-1,2,4-triazole, a silver salt of 2-mercaptobenzimidazole, a silver salt of 2-mercapto-5-aminothiadiazole, a silver salt of 2-(2-ethylglycolamido)benzothiazole, a silver salt of thioglycolic acid such as a silver salt of a S-alkylthioglycolic acid (wherein the alkyl group has from 12 to 22 carbon atoms) as described in Japanese Patent Application No. 28221/73, a silver salt of a dithiocarboxylic acid such as a silver salt of dithioacetic acid, a silver salt of thioamide, a silver salt of S-carboxylic-1-methyl-2-phenyl-4-thiopyridine, a silver salt of mercaptotriazine, a silver salt of 2-mercaptobenzoxazole, a silver salt as described in U.S. Pat. No. 4,123,274, for example, a silver salt of 1,2,4-mercaptothiazole derivative such as a silver salt of 3-amino-S-benzylthio-1,2,4-thiazole, a silver salt of a thione compound such as a silver salt of 3-(2-carboxyethyl)-4-methyl-4-thiazoline-2-thione as disclosed in U.S. Pat. No. 3,201,678.

Furthermore, an auxiliary silver salt of a compound containing an imino group can be used. Preferred examples of these compounds include a silver salt of benzothiazole and a derivative thereof, as described in Japanese Patent Application Nos. 30270/69 and 18146/70, for example, a silver salt of benzothiazole such as silver salt of methylbenzotriazole, etc., a silver salt of a halogen-substituted benzotriazole, such as a silver salt of 5-chlorobenzotriazole, etc., a silver salt of 1,2,4-triazole, of 1H-tetrazole as described in U.S. Pat. No. 4,220,709, a silver salt of imidazole and an imidazole derivative, and the like.

Additional auxiliary silver salts, silver half soaps, of which an equimolar blend of silver behenate and behenic acid, prepared by precipitation from aqueous solution of the sodium salt of commercial behenic acid and analyzing about 14 percent silver, represents a preferred example. Transparent sheet constructions made on transparent film backing require a transparent coating and, for this purpose the silver behenate full soap, containing not more than about 4 or 5 percent of free behenic acid and analyzing at about 25 percent silver may be used.

The method used for making silver soap dispersions is well known in the art and is disclosed in *Research Disclosure* April 1983 (22812), *Research Disclosure* October 1983 (23419) and U.S. Pat. No. 3,985,565.

The silver halide may be pre-formed and mixed with the silver-carboxylate/1,2-diazine compound and my auxiliary organic silver salt in a binder to prepare a coating solution. It is also effective to blend the silver halide, the a silver-carboxylate/ 1,2-diazine coordination compound, and any auxiliary organic silver salt in a bah mill for a long period of time. Materials of this type are often referred to as "pre-formed emulsions." It is also effective to use an in situ process which comprises adding a halogen-containing compound to the silver-carboxylate/1,2-diazine coordination compound and any auxiliary organic silver salt to partially convert the silver of the silver-carboxylate/1,2-diazine coordination compound and any organic silver salt to silver halide.

Methods of preparing these silver halide and auxiliary organic silver salts and manners of blending them are described in *Research Disclosure*, item No. 17029, Japanese patent applications No. 32928/75 and 42529/76, U.S. Pat. No. 3,700,458, and Japanese patent applications Nos. 13224/74 and 17216/75.

Pre-formed silver halide emulsions in the construction of this invention can be unwashed or washed to remove soluble salts. In the latter case the soluble salts can be removed by chill-setting and leaching or the emulsion can be coagulation washed, e.g., by the procedures described in Hewitson, et al., U.S. Pat. No, 2,618,556; Yutzy et al., U.S. Pat. No. 2,614, 928; Yackel, U.S. Pat. No. 2,565,418; Hart et al., U.S. Pat. No. 3,241,969; and Waller et al., U.S. Pat. No. 2,489,341. The silver halide grains may have any crystalline habit including, but not limited to, cubic, tetrahedral, orthorhombic, tabular, laminar, platelet, etc.

The silver halide and the non-photosensitive reducible silver source material that form a starting point of development should be in reactive association. By "reactive association" is meant that they should be in the same layer, in adjacent layers, or in layers separated from each other by an intermediate layer having a thickness of less than 1 micrometer (1 µm). It is preferred that the silver halide and the non-photosensitive reducible silver source material be present in the same layer.

Photothermographic emulsions containing pre-formed silver halide in accordance with this invention can be sensitized with chemical sensitizers, or with spectral sensitizers as described above.

The total amount of non-photosensitive, reducible source of silver (silver-carboxylate/1,2-diazine coordination compound and optionally, auxiliary organic silver salt compounds) is preferably present in an amount of from 15 to 70 percent by weight of the emulsion layer. It is more preferably present at a level of 30 to 55 percent by weight of the emulsion layer.

When used in photothermographic elements of the present invention, the auxiliary organic silver salt is a silver salt which is comparatively stable to light, but forms a silver image when heated to 80° C. or higher in the presence of an exposed photocatalyst (such as silver halide) and a reducing agent.

When used in thermographic elements of the present invention, the auxiliary organic silver salt is a silver salt which is comparatively stable to light, but forms a silver image when heated to 80° C. or higher in the presence of a reducing agent.

The Reducing Agent for the Non-Photosensitive Reducible Silver Source

When used in black-and-white photothermographic and thermographic constructions the present invention comprises a reducing agent for the non-photosensitive reducible silver source material.

The reducing agent for the organic silver salt may be any material, preferably organic material, that can reduce silver ion to metallic silver. Conventional photographic developers such as methyl gallate, hydroquinone, substituted-hydroquinones, hindered phenols, catechol, pyrogallol, ascorbic acid, ascorbic acid derivatives, leuco dyes, etc. Hindered phenol reducing agents are preferred.

A wide range of reducing agents has been disclosed in dry silver systems including amidoximes such as phenylamidoxime, 2-thienylamidoxime and p-phenoxyphenylamidoxime, azines (e.g., 4-hydroxy-3,5-dimethoxybenzaldehydeazine); a combination of aliphatic carboxylic acid aryl hydrazides and ascorbic acid, such as 2,2'-bis(hydroxymethyl)propionylbetaphenyl hydrazide in combination with ascorbic acid; a combination of polyhydroxybenzene and hydroxylamine, a reductone and/or a hydrazine, e.g., a combination of hydroquinone and bis(ethoxyethyl)hydroxylamine, piperidinohexose reductone or formyl-4-methylphenylhydrazine, hydroxamic acids such as phenylhydroxamic acid, p-hydroxyphenylhydroxamic acid, and o-alaninehydroxamic acid; a combination of azines and sulfonamidophenols, e.g., phenothiazine and 2,6-dichloro-4-benzenesulfonamidophenol; α-cyanophenylacetic acid derivatives such as ethyl α-cyano-2-methylphenylacetate, ethyl α-cyano-phenylacetate; bis-o-naphthols as illustrated by 2,2'-dihydroxyl-1-binaphthyl, 6,6'-dibromo-2,2'-dihydroxy-1,1'-binaphthyl, and bis(2-hydroxy-1-naphthyl)methane; a combination of bis-o-naphthol and a 1,3-dihydroxybenzene derivative, (e.g., 2,4-dihydroxybenzophenone or 2,4-dihydroxyacetophenone); 5-pyrazolones such as 3-methyl-1-phenyl-5-pyrazolone; reductones as illustrated by dimethylaminohexose reductone, anhydrodihydroaminohexose reductone, and anhydrodihydro-piperidone-hexose reductone; sulfamidophenol reducing agents such as 2,6-dichloro-4-benzenesulfonamidophenol, and p-benzenesulfonamidophenol; 2-phenylindane-1,3-dione and the like; chromans such as 2,2-dimethyl-7-t-butyl-6-hydroxychroman; 1,4-dihydropyridines such as 2,6-dimethoxy-3,5-dicarbethoxy-1 4-dihydropyridine; bisphenols, e.g., bis(2-hydroxy-3-t-butyl-5-methylphenyl)methane; 2,2-bis(4-hydroxy-3-methylphenyl)propane; 4,4-ethylidene-bis(2-t-butyl-6-methylphenol); and 2,2-bis(3,5-dimethyl-4-hydroxyphenyl)propane; ascorbic acid derivatives, e.g., 1-ascorbylpalmitate, ascorbylstearate and unsaturated aldehydes and ketones; 3-pyrazolidones; and certain indane-1,3-diones.

The reducing agent should be present as 1 to 10% by weight of the imaging layer. In multilayer constructions, if the reducing agent is added to a layer other than an emulsion layer, slightly higher proportions, of from about 2 to 15 wt %, tend to be more desirable.

The Optional Dye-Forming or Dye-Releasing Material

As noted above, the reducing agent for the reducible source of silver may be a compound that can be oxidized directly or indirectly to form a dye or to release a pre-formed dye.

The dye-forming or releasing material may be any colorless or lightly colored compound that can be oxidized to a colored form, when heated, preferably to a temperature of from about 80° C. to about 250° C. (176° F. to 482° F.) for a duration of from about 0.5 to about 300 seconds. When used with a dye- or image-receiving layer, the dye can diffuse through emulsion layers and interlayers into the image-receiving layer of the element of the invention.

Leuco dyes are one class of dye-releasing material that form a dye upon oxidation. Any leuco dye capable of being oxidized by silver ion to form a visible image can be used in the present invention. Leuco dyes that are both pH sensitive and oxidizable can be used, but are not preferred. Leuco dyes that are sensitive only to changes in pH are not included within scope of dyes useful in this invention because they are not oxidizable to a colored form.

As used herein, the term "change in color" includes: (1) a change from an uncolored or lightly colored state (optical density less than 0.2) to a colored state (an increase in optical density of at least 0.2 units); and (2) a substantial change in hue.

Representative classes of leuco dyes that are suitable for use in the present invention include, but are not limited to, bisphenol and bisnaphthol leuco dyes, phenolic leuco dyes, indoaniline leuco dyes, imidazole leuco dyes, azine leuco dyes, oxazine leuco dyes, diazine leuco dyes, thiazine leuco dyes, and triarylmethane leuco dyes. Preferred classes of dyes are described in U.S. Pat. Nos. 4,460,681 and 4,594,307.

One class of leuco dyes useful in this invention are those derived from imidazole dyes. Imidazole leuco dyes are described in U.S. Pat. No. 3,985,565.

Another class of leuco dyes useful in this invention are those derived from so-called "chromogenic dyes." These dyes are prepared by oxidative coupling of a p-phenylenediamine with a phenolic or anilinic compound. Leuco dyes of this class are described in U.S. Pat. No. 4,594,307. Leuco chromogenic dyes having short chain carbamoyl protecting groups are described in copending application U.S. Ser. No. 07/939,093, incorporated herein by reference.

A third class of dyes useful in this invention are "aldazine" and "ketazine" dyes. Dyes of this type are described in U.S. Pat. Nos. 4,587,211 and 4,795,697.

Another class of leuco dyes are reduced forms of dyes having a diazine, oxazine, or thiazine nucleus. Leuco dyes of this type can be prepared by reduction and acylation of the color-bearing dye form. Methods of preparing leuco dyes of this type are described in Japanese Pat. No. 52-89131 and U.S. Pat. Nos. 2,784,186; 4,439,280; 4,563,415; 4,570,171; 4,622,395; and 4,647,525.

Another class of dye-releasing materials that form a dye upon oxidation are known as preferred-dye-release (PDR) or redox-dye-release (RDR) materials. In these materials, the reducing agent for the organic silver compound releases a pre-formed dye upon oxidation. Examples of these materials are disclosed in Swain, U.S. Pat. No. 4,981,775.

Also useful are neutral, phenolic leuco dyes such as 2-(3,5-di-t-butyl-4-hydroxyphenyl)-4,5-diphenylimidazole, or bis(3,5-di-t-butyl-4-hydroxy-phenyl)phenylmethane. Other phenolic leuco dyes useful in practice of the present invention are disclosed in U.S. Pat. Nos. 4,374,921; 4,460,681; 4,594,307; and 4,782,010.

Other leuco dyes may be used in imaging layers as well, for example, benzylidene leuco compounds, cited in U.S. Pat. No. 4,923,792. The reduced form of the dyes should absorb less strongly in the visible region of the electromagnetic spectrum and be oxidized by silver ions back to the original colored form of the dye. Benzylidene dyes have extremely sharp spectral characteristics giving high color purity of low gray level. The dyes have large extinction coefficients, typically on the order of $10^4$ to $10^5$ mole-cm liter$^{-1}$, and possess good compatibility and heat stability. The dyes are readily synthesized and the reduced leuco forms of the compounds are very stable. Leuco dyes such as hose disclosed in U.S. Pat. Nos. 3,442,224; 4,021,250; 4,022,617; and 4,368,247 are also useful in the present invention.

The dyes formed from the leuco dye in the various color-forming layers should, of course, be different. A difference of at least 60 nm in reflective maximum absorbance is preferred. More preferably, the absorbance maximum of dyes formed will differ by at least 80–100 nm. When three dyes are to be formed, two should preferably differ by at least these minimums, and the third should preferably differ from at least one of the other dyes by at least 150 nm, and more preferably, by at least 200 nm. Any leuco dye capable of being oxidized by silver ion to form a visible dye is useful in the present invention as previously noted.

The dyes generated by the leuco compounds employed in the elements of the present invention are known and are disclosed, for example, in *The Colour Index*; The Society of Dyes and Colourists: Yorkshire, England, 1971; Vol. 4, p. 4437; and Venkataraman, K. *The Chemistry of Synthetic Dyes*; Academic Press: New York, 1952; Vol. 2, p. 1206; and U.S. Pat. No. 4,478,927.

Leuco dye compounds may readily be synthesized by techniques known in the art. Suitable methods are disclosed, for example, in: F. X. Smith et al. *Tetrahedron Lett.* 1983, 24(45), 4951–4954; X. Huang., L. Xe, *Synth. Commun.* 1986, 16(13) 1701–1707; H. Zimmer et al. *J. Org. Chem.* 1960, 25, 1234–5; M. Sekiya et al. *Chem. Pharm. Bull.* 1972, 20(2),343; and T. Sohda et al. *Chem. Pharm. Bull.* 1983, 31(2) 560–5; H. A. Lubs *The Chemistry of Synthetic Dyes and Pigments*; Hafner; New York, N.Y.; 1955 Chapter 5; in H. Zoilinger *Color Chemistry: Synthesis, Properties and Applications of Organic Dyes and Pigments*; VCH; New York, N.Y.; pp. 67–73, 1987, and in U.S. Pat. No. 5,149,807; and EPO Laid Open Application No. 0,244,399.

Further, as other imaged forming materials, materials where the mobility of the compound having a dye part changes as a result of an oxidation-reduction reaction with silver halide, or an organic silver salt at high temperature can be used, as described in Japanese Pat. Application No. 165054 (1984). Many of the above-described materials are materials wherein an image-wise distribution of mobile dyes corresponding to exposure is formed in the photosensitive material by heat development. Processes of obtaining visible images by transferring the dyes of the image to a dye-fixing material (diffusion transfer) have been described in the above-described cited patents and Japanese Patent Application Nos. 168,439 (1984) and 182,447 (1984).

Still further the reducing agent may be a compound that releases a conventional photographic dye coupler or developer upon oxidation as is known in the art. When the heat developable, photosensitive element used in this invention is heat developed in a substantially water-free condition after or simultaneously with imagewise exposure, a mobile dye image is obtained simultaneously with the formation of a silver image either in exposed areas or in unexposed areas with exposed photosensitive silver halide.

The total amount of optional leuco dye used as a reducing agent utilized in the present invention should preferably be in the range of 0.5–25 weight percent, and more preferably, in the range of 1–10 weight percent, based upon the total weight of each individual layer in which the reducing agent is employed.

The Binder

The photosensitive silver halide (when used), the non-photosensitive reducible source of silver (i.e., the silver-carboxylate/1,2-diazine coordination compound), the reducing agent, the optional leuco dye, and other addenda used in the present invention are generally added to at least one binder as described herein below.

The binder(s) that can be used in the present invention can be employed individually or in combination with one another. It is preferred that the binder be selected from polymeric materials, such as, for example, natural and synthetic resins and that the binder be sufficiently polar to hold the other ingredients of the emulsion in solution or suspension. The binder may be hydrophilic or hydrophobic.

A typical hydrophilic binder is a transparent or translucent hydrophilic colloid, examples of which include a natural substance, for example, a protein such as gelatin, a gelatin derivative, a cellulose derivative, etc.; a polysaccharide such as starch, gum arabic, pullulan, dextrin, etc.; and a synthetic polymer, for example, a water-soluble polyvinyl compound such as polyvinyl alcohol, polyvinyl pyrrolidone, acrylamide polymer, etc. Another example of a hydrophilic binder is a dispersed vinyl compound in latex form which is used for the purpose of increasing dimensional stability of a photographic element.

Examples of typical hydrophobic binders are polyvinyl acetals, polyvinyl chloride, polyvinyl acetate, cellulose acetate, polyolefins, polyesters, polystyrene, polyacrylonitrile, polycarbonates, methacrylate copolymers, maleic anhydride ester copolymers, butadiene-styrene copolymers, and the like. Copolymers, e.g. terpolymers, are also included in the definition of polymers. The polyvinyl acetals, such as polyvinyl butyral and polyvinyl formal, and vinyl copolymers such as polyvinyl acetate and polyvinyl chloride are particularly preferred. The binders can be used individually or in combination with one another. Although the binder may be hydrophilic or hydrophobic, it is preferably hydrophobic.

The binders are generally used at a level of from about 20 to about 80% by weight of the emulsion layer, and preferably, from about 30 to about 55% by weight. Where the proportions and activities of leuco dyes require a particular developing time and temperature, the binder should be able to withstand those conditions. Generally, it is preferred that the binder not decompose or lose its structural integrity at 200° F. (90° C.) for 30 seconds, and more preferred that it not decompose or lose its structural integrity at 300° F. (149° C.) for 30 seconds.

Optionally, these polymers may be used in combination of two or more thereof. Such a polymer is used in an amount sufficient to carry the components dispersed therein, that is, within the effective range of the action as the binder. The effective range can be appropriately determined by one skilled in the art.

Photothermographic and Thermographic Formulations

The formulation for the photothermographic and thermographic emulsion layer can be prepared by dissolving and dispersing the binder, the photosensitive silver halide (when used), the non-photosensitive reducible source of silver; comprising a silver-carboxylate/1,2-diazine coordination compound; the reducing agent for the non-photosensitive reducible silver source (as, for example, the. optional leuco dye), and optional additives, in an inert organic solvent, such as, for example, toluene, 2-butanone, or tetrahydrofuran.

The use of "toners" or derivatives thereof which improve the image, is highly desirable, but is not essential to the element. Toners may be present in amounts of from 0.01 to 10 percent by weight of the emulsion layer, preferably from 0.1 to 10 percent by weight. Toners are well known materials in the photothermographic art as shown in U.S. Pat. Nos. 3,080,254; 3,847,612; and 4,123,282.

Examples of toners include phthalimide and N-hydroxyphthalimide; cyclic imides such as succinimide, pyrazoline-5-ones, and a quinazolinone, 1-phenylurazole, 3-phenyl-2-pyrazoline-5-one, quinazoline and 2,4-thiazolidinedione; naphthalimides such as N-hydroxy-1,8-naphthalimide; cobalt complexes such as cobaltic hexamine trifluoroacetate; mercaptans as illustrated by 3-mercapto-1, 2,4-triazole, 2,4-dimercaptopyrimidine, 3-mercapto-4,5-diphenyl-1,2,4-triazole and 2,5-dimercapto-1, 3,4-thiadiazole; N-(aminomethyl)aryldicarboximides, e.g. (N,N-dimethylaminomethyl)phthalimide, and N-(dimethylaminomethyl)naphthalene-2,3-dicarboximide; and a combination of blocked pyrazoles, isothiuronium derivatives and certain photobleach agents, e.g., a combination of N,N'-hexamethylene-bis(1-carbamoyl-3,5-dimethylpyrazole), 1,8-(3,6-diaza-octane)bis(isothiuronium)trifluoroacetate and 2-(tribromomethylsulfonyl benzothiazole); and merocyanine dyes such as 3-ethyl-5-[(3-ethyl-2-benzothiazolinylidene)-1-methyl-ethylidene]-2-thio-2,4-o-azolidinedione; phthalazinone, phthalazinone derivatives or metal salts or these derivatives such as 4-(1-naphthyl)phthalazinone, 6-chlorophthalazinone, 5,7-dimethoxyphthalazinone, and 2,3-dihydro-1,4-phthalazinedione; a combination of phthalazine plus one or more phthalic acid derivatives, e.g., phthalic acid, 4-methylphthalic acid, 4-nitrophthalic acid, and tetrachlorophthalic anhydride; quinazolinediones, benzoxazine or naphthoxazine derivatives; rhodium complexes functioning not only as tone modifiers but also as sources of halide ion for silver halide formation in situ, such as ammonium hexachlororhodate (III), rhodium bromide, rhodium nitrate and potassium hexachlororhodate (III); inorganic peroxides and persulfates, e.g., ammonium peroxydisulfate and hydrogen peroxide; benzoxazine-2,4-diones such as 1,3-benzoxazine-2,4-dione, 8-methyl- 1,3-benzoxazine-2,4-dione, and 6-nitre-1,3-benzoxazine-2,4-dione; pyrimidines and asym-triazines, e.g., 2,4-dihydroxypyrimidine, 2-hydroxy-4-aminopyrimidine, and azauracil, and tetrazapentalene derivatives, e.g., 3,6-dimercapto-1,4-diphenyl-1H, 4H-2,3a,5,6a-tetrazapentalene, and 1,4-di(o-chlorophenyl)-3,6-dimercapto-1H, 4H-2,3a,5,6a-tetrazapentalene.

When used in photothermographic elements, the photothermographic elements used in this invention may be further protected against the additional production of fog and can be stabilized against loss of sensitivity during keeping. While not necessary for the practice of the invention, it may be advantageous to add mercury (II) salts to the emulsion layer(s) as an antifoggant. Preferred mercury (II) salts for this purpose are mercuric acetate and murcuric bromide.

Suitable antifoggants and stabilizers, which can be used alone or in combination, include the thiazolium salts described in U.S. Pat. Nos. 2,131,038 and U.S. Pat. No.

2,694,716; the azaindenes described in U.S. Pat. Nos. 2,886, 437 and 2,444,605; the mercury salts described in U.S. Pat. No. 2,728,663; the urazoles described in U.S. Pat. No. 3,287,135; the sulfocatechols described in U.S. Pat. No. 3,235,652; the oximes described in British Patent No. 623, 448; the polyvalent metal salts described in U.S. Pat. No. 2,839,405; the thiuronium salts described in U.S. Pat. He. 3,220,839; and palladium, platinum and gold salts described in U.S. Pat. Nos. 2,566,263 and 2,597,915.

Photothermographic and thermographic elements of the invention may contain plasticizers and lubricants such as polyalcohols, e.g., glycerin and diols of the type described in U.S. Pat. No. 2,960,404; fatty acids or esters such as those described in U.S. Pat. Nos. 2,588,765 and 3,121,060; and silicone resins such as those described in British Patent No. 955,061.

The photothermographic and thermographic elements of the present invention may include image dye stabilizers.

4,460,681.

Development conditions will vary, depending on the construction used, but will typically involve heating the imagewise exposed material at a suitably elevated temperature.

When used in a photothermographic element, the latent image obtained after exposure of the heat-sensitive construction can be developed by heating the material at a moderately elevated temperature of, for example, about 80° C. to about 250° C., preferably from about 120° C. to about 200° C., for a sufficient period of time, generally from 1 second tO 2 minutes. Heating may be carried out by the typical heating means such as a hot plate, an iron, a hot roller, a heat generator using carbon or titanium white, or the like.

In some methods, the development is carried out in two steps. Thermal development takes place at a higher temperature, e.g. about 150° C. for about 10 seconds, followed by thermal diffusion at a lower temperature, e.g. 80° C., in cellulose nitrate film, cellulose ester film, polyvinyl acetal film, polycarbonate film and related or resinous materials, as well as glass, paper, metal and the like. Typically, a flexible support is employed, especially a paper support, which can be partially acetylated or coated with baryta and/or an α-olefin polymer, particularly a polymer of an alpha-olefin containing 2 to 10 carbon atoms such as polyethylene, polypropylene, ethylene-butene copolymers, and the like. Preferred polymeric materials for the support include polymers having good heat stability, such as polyesters. A particularly preferred polyester is poly(ethylene terephthalate).

The substrate with backside resistive heating layer may also be used in color photothermographic imaging systems such as shown in U.S. Pat. Nos. 4,460,681 and 4,374,921.

The Image-Receiving Layer

When the reactants and reaction products of photothermographic and thermographic systems that contain compounds capable of being oxidized to form or release a dye remain in contact after imaging, several problems can result. For example, thermal development often forms turbid and hazy color images because of dye contamination by the reduced metallic silver image on the exposed area of the emulsion. In addition, the resulting prints tend to develop color in unimaged background areas. This "background stain" is caused by slow reaction between the dye-forming or dye-releasing compound and reducing agent during storage. It is therefore desirable to transfer the dye formed upon imaging to a receptor, or image-receiving layer.

Thus, the photothermographic or thermographic element may further comprise an image-receiving layer. Images derived from the photothermographic elements employing compounds capable of being oxidized to form or release a dye, such as, as for example, leuco dyes, are typically transferred to an image-receiving layer.

If used, dyes generated during thermal development of light-exposed regions of the emulsion layers migrate under development conditions into the an image-receiving or dye-receiving layer wherein they are retained. The dye-receiving layer may be composed of a polymeric material having affinity for the dyes employed. Necessarily, it will vary depending on the ionic or neutral characteristics of the dyes.

The image-receiving layer of ibis invention can be any flexible or rigid, transparent layer made of thermoplastic polymer. The image-receiving layer preferably has a thickness of at least 0.1 μm more preferably from about 1 to about 10 μm, and a glass transition temperature ($T_g$) of from about 20° C. to about 200° C. In the present invention, any thermoplastic polymer or combination of polymers can be used, provided the polymer is capable of absorbing and fixing the dye. Because the polymer acts as a dye mordant, no additional fixing agents are required. Thermoplastic polymers that can be used to prepare the image-receiving layer include polyesters, such as polyethylene terephthalates; polyolefins, such as polyethylene; cellulosics, such as cellulose acetate, cellulose butyrate, cellulose propionate; polystyrene; polyvinyl chloride; polyvinylidine chloride; polyvinyl acetate; copolymer of vinyl chloride-vinyl acetate; copolymer of vinylidene chloride-acrylonitrile; copolymer of styrene-acrylonitrile; and the like.

The optical density of the dye image and even the actual color of the dye image in the image-receiving layer is very much dependent on the characteristics of the polymer of the image-receiving layer, which acts as a dye mordant, and, as such, is capable of absorbing and fixing the dyes. A dye image having a reflection optical density in the range of from 0.3 to 3.5 (preferably, from 1.5 to 3.5) or a transmission optical density in the range of from 0.2 to 2.5 (preferably, from 1.0 to 2.5) is desirable.

The image-receiving layer can be formed by dissolving at least one thermoplastic polymer in an organic solvent (e.g., 2-butanone, acetone, tetrahydrofuran) and applying the resulting solution to a support base or substrate by various coating methods known in the art, such as curtain coating, extrusion coating, dip coating, air-knife coating, hopper coating, and any other coating method used for coating solutions. After the solution is coated, the image-receiving layer is dried (e.g., in an oven) to drive off the solvent. The image-receiving layer may be strippably adhered to the photothermographic clement. Strippably image-receiving layers are described in U.S. Pat. No. 4,594,307, incorporated herein by reference.

Selection of the binder and solvent to be used in preparing the emulsion layer significantly affects the strippability of the image-receiving layer from the photosensitive element. Preferably, the binder for the image-receiving layer is impermeable to the solvent used for coating the emulsion layer and is incompatible with the binder used for the emulsion layer. The selection of the preferred binders and solvents results in weak adhesion between the emulsion layer and the image-receiving layer and promotes good strippability of the emulsion layer.

The photothermographic element can also include coating additives to improve the strippability of the emulsion layer. For example, fluoroaliphatic polyesters dissolved in ethyl acetate can be added in an amount of from about 0.02 to about 0.5 weight percent of the emulsion layer, preferably from about 0.1 to about 0.3 weight percent. A representative example of such a fluoroaliphatic polyester is "Fluorad FC 431", (a fluorinated surfactant available from 3M Company, St. Paul, Minn.). Alternatively, a coating additive can be added to the image-receiving layer in the same weight range to enhance strippability. No solvents need to be used in the stripping process. The strippable layer preferably has a delaminating resistance of 1 to 50 g/cm and a tensile strength at break greater than, preferably at least two times greater than, its delaminating resistance.

Preferably, the image-receiving layer is adjacent to the emulsion layer in order to facilitate transfer of the dye that forms after the imagewise. exposed emulsion layer is subjected to thermal development, for example, in a heated shoe-and-roller-type heat processor.

Photothermographic multi-layer constructions containing blue-sensitive emulsions containing a yellow leuco dye may be overcoated with green-sensitive emulsions containing a magenta leuco dye, These layers may in turn be overcoated with a red-sensitive emulsion layer containing a cyan leuco dye. Imaging and heating form the yellow, magenta, and cyan images in an imagewise fashion. The dyes so formed may migrate to an image-receiving layer. The image-receiving layer may be a permanent part of the construction or may be removable, "i.e., strippably adhered," and subsequently peeled from the construction. Color-forming layers may be maintained distinct from each other by the use of functional or non-functional barrier layers between the various photosensitive layers as described in U.S. Pat. No. 4,460,681. False color address, such as that shown in U.S. Pat. No. 4,619,892, may also be used rather than blue-yellow, green-magenta, or red-cyan relationships between sensitivity and dye formation.

In another embodiment, the colored dye released in the emulsion layer can be transferred onto a separately coated image-receiving sheet by placing the exposed emulsion layer in intimate face-to-face contact with the image-receiving sheet and heating the resulting composite construction. Good results can be achieved in this second embodiment when the layers are in uniform contact for a period of time of from 0.5 to 300 seconds at a temperature of from about 80° C. to about 220° C.

Alternatively, a multi-colored image may be prepared by superimposing in register a single image-receiving sheet successively with two or more imagewise exposed photothermographic or thermographic elements, each of which release a dye of a different color, and heating to transfer the released dyes as described above. This method is particularly suitable for the production of color proofs especially when the dyes released have hues which match the internationally-agreed standards for color reproduction (SWOP colors). Dyes with this property are disclosed in U.S. Pat. No. 5,023,229. In this embodiment, the photothermographic or thermographic element preferably comprise compounds capable of being oxidized tO release a pre-formed dye as this enables the image dye absorptions to be tailored more easily to particular requirements of the imaging system. When used in a photothermographic element, the elements are preferably all sensitized to the same wavelength range regardless of the color of the dye released. For example, the elements may be sensitized to ultra-violet radiation with a view toward contact exposure on conventional printing frames, or they may be sensitized to larger wavelengths, especially red or near infra-red to enable digital address by lasers.

Objects and advantages of this invention will now be illustrated by the following examples, but the particular materials and amounts thereof recited in these examples, as well as other conditions and details, should not be construed to unduly limit this invention. All percentages are by weight unless otherwise indicated.

EXAMPLES

All materials used in the following examples were readily available from standard commercial sources such as Aldrich Chemical Co. (Milwaukee, Wis.) unless otherwise specified. The following additional terms and materials were used.

Butvar™ B-72 is a poly(vinyl butyral) available from Monsanto Company, St. Louis, Mo.

PET is poly(ethylene terephthalate).

CAO-5 is an antioxidant available from Rohm and Haas, Philadelphia, Pa. and has the structure shown below:

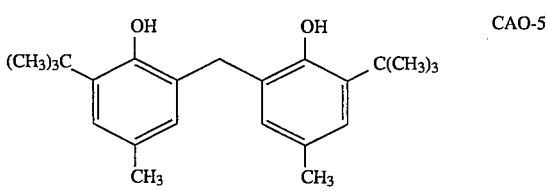

EXAMPLE 1

Preparation of coordination compounds:

Preparation of $[Ag(PHZ)(O_2CCH_3)(H_2O)_2]_2$: Mixing stoichiometric amounts of PHZ and silver acetate under ambient conditions (room temperature and subdued laboratory light) in water yielded colorless, air and light stable crystals.

Preparation of other carboxylate derivatives $[Ag(PHZ)(O_2CR^1)]_2$: 1:1 mole ratios of reactants were dissolved or dispersed in water, stirred for one hour, filtered, washed and air dried in tile dark. For compounds of $[Ag(PHZ)(O_2CR^1)]_2$ having water solubility, the filtrates were allowed to slowly evaporate to yield highly crystalline solids. In all cases, elemental microanalysis confirmed the presence of the PHZ in the silver-carboxylate coordination compound.

Evaluation of coordination compounds in a black-and-white construction:

The silver-carboxylate/1,2-diazine compounds were milled in the dark (0.7 g in 7.0g of 5% Butvat™ B-72 in ethanol), coated 3 mils wet, oven dried at 80° C. for 2 minutes and cut into strips. The strips were streaked with a 20% solution of CAO-5 in ethanol and, air dried. The samples were placed on a thermal wedge (Reichert Hot Bench™) for 6 seconds and immediately thermally quenched on a room temperature heat sink. The temperatures for the onset of thermal imaging and approximate $D_{max}$ were measured. The results are shown in the table below and demonstrate the constructions possible for the thermally activated imaging properties of these novel silver coordination complexes. Other phenolic developers in addition to CAO-5, such as hydroquinone, have been found to produce thermally generated images with these materials.

| $R^1$ in $[Ag(PHZ)(O_2CR^1)]_2$ | $T_{onset}$ °C. | $T_{Dmax}$ °C. | Image Color |
| --- | --- | --- | --- |
| —$CH_2CH_2CO_2H$ | 100 | 120 | brown-black |
| —$CF_3$ | 110 | 130 | tan |
| —$CH_2NH_2$ | RT | | dark red-brown |
| —$C(CH_3)_3$ | RT | | dark brown |
| —$(CH_2)_4CH_3$ | RT | | black |
| —$(CH_2)_{12}CH_3$ | 100 | 120 | dark brown |
| —$(CH_2)_{11}OH$ | 100 | 120 | dark brown |
| -(4-$CH_3)C_6H_3CO_2AgPHZ$ | RT | | purple-black |
| —$C_6H_4$-p-CN | 105 | 140 | brown-black |
| —$C_6H_4$-p-$C(CH_3)_3$ | 90 | 135 | dark brown |

RT = Room Temperature

EXAMPLE 2

Evaluation of coordination compounds in a color-imaging Construction

The silver-carboxylate/1,2-diazine compounds were milled in the dark (0.7 g in 7.0 g of 5% Butvat™ B-72 in ethanol), coated 3 mils wet, oven dried at 80° C. for 2 minutes and cut into strips. The strips were streaked with a 2% solution of the leuco dye in ethanol or tetrahydrofuran and air dried. The samples were placed on a thermal wedge (Reicheft Hot Bench™) for 6 seconds and immediately thermally quenched on a heat sink (at room temperature). The temperatures for the onset of thermal imaging and approximate $D_{max}$ were measured. The results are shown in the attached table and demonstrate the simple constructions possible for the thermally activated imaging properties of these novel silver coordination compounds for thermographic color imaging.

The leuco dyes tested have the following structures:

Leuco Dye-1 is an leuco oxazine dye described in U.S. Pat. No. 4,782,010 and has the formula shown below.

Leuco Dye-2 is a leuco benzimidazole dye and is described in U.S. Pat. No. 3,985,565.

Leuco Dye-3 is a bis-phenol leuco dye and is described in U.S. Pat. No. 4,535,056.

Leuco Dye-4 is a leuco oxazine dye described in U.S. Pat. Nos. 4,587,211 and 4,795,697 and has the formula shown below.

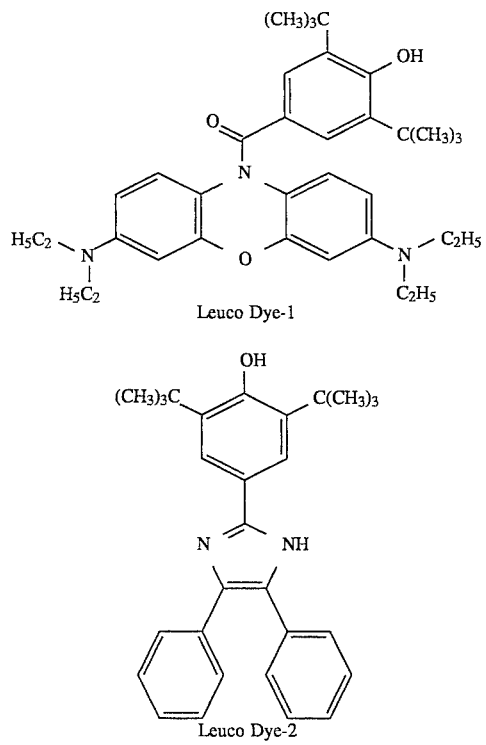

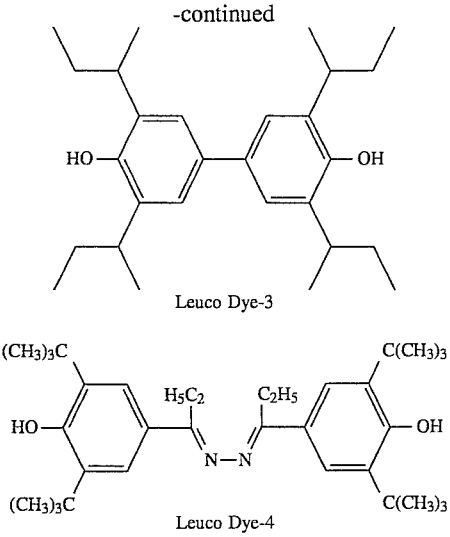

| $R^1$ in $[Ag(PHZ)(O_2CR^1)]_2$ | Dye | $T_{onset}$ °C. | $T_{Dmax}$ °C. | Image Color |
|---|---|---|---|---|
| —$(CH_2)_{11}OH$ | Leuco Dye-1 | 115 | 135 | blue-green |
| —$CH_2CH_2CO_2H$ | " | 89 | 130 | " |
| —$C_6H_4$-p-CN | " | 114 | 133 | " |
| —$C_6H_4$-p-t-butyl | " | 110 | 130 | " |
| —$(CH_2)_4CH_3$ | " | RT | | " |
| —$(CH_2)_{11}OH$ | Leuco Dye-2 | 100 | 115 | yellow |
| —$CH_2CH_2CO_2H$ | " | 110 | 121 | " |
| —$C_6H_4$-p-CN | " | 120 | 140 | " |
| —$C_6H_4$-p-t-butyl | " | 120 | 140 | " |
| —$(CH_2)_4CH_3$ | " | 115 | 135 | " |
| —$(CH_2)_{11}OH$ | Leuco Dye-4 | 100 | 135 | magenta |
| —$CH_2CH_2CH_2H$ | " | 100 | 115 | " |
| —$C_6H_4$-p-CN | " | 110 | 127 | " |
| —$C_6H_4$-p-t-butyl | " | 120 | >150 | " |
| —$(CH_2)_4CH_3$ | " | 90 | 119 | " |
| —$(CH_2)_{11}OH$ | Leuco Dye-3 | 88 | 110 | yellow |
| —$CH_2CH_2CO_2H$ | " | 90 | 124 | " |
| —$C_6H_4$-p-CN | " | 120 | 132 | " |
| —$C_6H_4$-p-t-butyl | " | 100 | 130 | " |
| —$(CH_2)_4CH_3$ | " | 80 | 100 | " |

RT = Room Temperature

Reasonable modifications and variations are possible from the foregoing disclosure without departing from either the spirit or scope of the present invention as defined by the claims.

What is claimed is:

1. A silver-carboxylate/1,2-diazine compound having the formula:

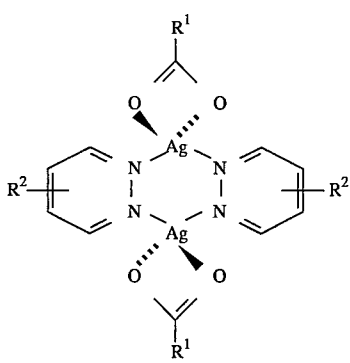

wherein:

R$^1$ is either an alkyl, aralkyl, cycloalkyl, or alkenyl group of up to 29 carbon atoms; or an aryl group of up to 14 carbon atoms; and and R$^2$ represents either hydrogen, an alkyl group, a cycloalkyl group fused to the 1,2-diazine ring, or the atoms necessary to complete a 6-membered aromatic ring fused to the 1,2-diazine ring;

wherein one or more of said groups of R$^1$ and R$^2$ may be substituted with hydroxyl, alkoxy, vinyl, phenyl, halogen, cyano, nitro, amino, or carboxyl.

2. The compound according to claim 1 wherein R$^1$ is either an alkyl, aralkyl, cycloalkyl, or alkenyl group of from 9 to 29 carbon atoms or an aryl group of up to 10 carbon atoms.

3. The compound according to claim 2 wherein R$^1$ is either an alkyl, aralkyl, cycloalkyl, or alkenyl group of from 14 to 27 carbon atoms.

4. The compound according to claim 1 wherein R$^2$ represents the atoms necessary to complete a 6-membered aromatic ring fused to a 1,2-diazine ring.

* * * * *